United States Patent
Fayram

(10) Patent No.: US 7,031,139 B1
(45) Date of Patent: Apr. 18, 2006

(54) STACKABLE CAPACITOR HAVING OPPOSED CONTACTS FOR AN IMPLANTABLE ELECTRONIC MEDICAL DEVICE

(75) Inventor: Timothy A. Fayram, Gilroy, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 543 days.

(21) Appl. No.: 10/313,510

(22) Filed: Dec. 5, 2002

(51) Int. Cl.
*H01G 9/04* (2006.01)
*H01G 2/10* (2006.01)

(52) U.S. Cl. ............... 361/508; 361/517; 361/528
(58) Field of Classification Search ........ 361/502–503, 361/508–509, 517–520, 538–539
See application file for complete search history.

(56) References Cited

U.S. PATENT DOCUMENTS

| | | |
|---|---|---|
| 5,131,388 A | 7/1992 | Pless et al. |
| 5,522,851 A | 6/1996 | Fayram |
| 5,737,181 A * | 4/1998 | Evans ............ 361/504 |
| 5,814,082 A | 9/1998 | Fayram et al. |
| 5,926,357 A | 7/1999 | Elias et al. |
| 5,930,109 A | 7/1999 | Fishler |
| 5,983,472 A | 11/1999 | Fayram et al. |
| 6,117,194 A | 9/2000 | Strange et al. |
| 6,377,442 B1 | 4/2002 | Strange et al. |
| 2002/0097550 A1 * | 7/2002 | Shimada et al. ........ 361/532 |

* cited by examiner

*Primary Examiner*—Eric W. Thomas
(74) *Attorney, Agent, or Firm*—Steven M. Mitchell

(57) ABSTRACT

An implantable cardioverter-defibrillator has a housing containing cardioverter-defibrillator circuitry and a capacitor assembly. The capacitor assembly includes at least two flat capacitors each having opposed major surfaces. Each capacitor has an anode contact at one major surface, and a cathode contact at the opposite major surface. The anode contact of one of the capacitors contacts the cathode contact of the other. Each capacitor contact may be a thin metal plate covering the entire surface of the capacitor, with each plate connected to corresponding interleaved cathode or anode flat sheets between the plates. A non-conductive perimeter may enclose the sheets and connect the plates to each other.

13 Claims, 6 Drawing Sheets

STACKABLE CAPACITOR HAVING OPPOSED CONTACTS FOR AN IMPLANTABLE ELECTRONIC MEDICAL DEVICE

FIELD OF THE INVENTION

This invention relates to electronic components for implantable medical devices, and more particularly to compact flat capacitors.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500–800V. The ICD operates by using sensors to detect a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart.

The volume of the device is an important characteristic, with small size being desired for patient comfort. Given this, it is important that device life not be sacrificed to achieve this, such as would occur if battery capacity were diminished to achieve a smaller size. Capacitors occupy a significant fraction of the device volume, and it is desirable to minimize the capacitor size without sacrificing the required charge storage capacity. Existing ICDs employ compact flat capacitors having a stack of highly etched anodes alternating with thin cathode foil layers (and separators between each cathode and anode.) A current capacitor design has a flat shape, with a peripheral profile shaped to fit efficiently within an ICD housing. An ICD contains two of these capacitors, overlaying each other in registration for a compact assembly. Each capacitor has a metal housing that Is connected to the cathode layers, while the anode layers are isolated from the housing, and connected to a conductive "feed through" element that penetrates the housing through an insulative sleeve that preserves the leak-proof nature of the housing while providing a connection to the anodes.

While generally effective, the current capacitor design has some space inefficiencies that increase device volume without increasing capacitance. The housing design and feed through element occupy more space than would be desired. In addition, the use of two capacitors requires wiring connections between them and to circuitry that occupy volume in the device housing. Moreover, these wiring connections are vulnerable to damage during assembly, and can reduce production yields and require scrapping of components if damage occurs.

The use of two capacitors is necessitated in current designs by the required voltage for therapy, and by the technology used to form the capacitor components. To achieve the 830 voltage range required, two capacitors are connected in series, each capacitor employing costly advanced technology including specialized high-gain anode etching and dielectric formation that provides 415V per unit. While less-advanced technology can provide 250–375V capacitors at a much lower cost, this may necessitate a third unit in the assembly, increasing the volume consumed by the capacitors with another case, feed-through, and interconnection wires.

SUMMARY OF THE INVENTION

The disclosed embodiment overcomes the limitations of the prior art by providing an implantable cardioverter-defibrillator (ICD). The ICD has a housing containing cardioverter-defibrillator circuitry and a capacitor assembly. The capacitor assembly includes at least two flat capacitors each having opposed major surfaces. Each capacitor has an anode contact at one major surface, and a cathode contact at the opposite major surface. The anode contact of one of the capacitors contacts the cathode contact of the other. Each capacitor contact may be a thin metal plate covering the entire surface of the capacitor, with each plate connected to corresponding interleaved cathode or anode flat sheets between the plates. A non-conductive perimeter may enclose the sheets and connect the plates to each other.

BRIEF DESCRIPTION OF THE DRAWINGS

Further features and advantages of the present invention may be more readily understood by reference to the following description taken in conjunction with the accompanying drawings, in which.

DETAILED DESCRIPTION OF A PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
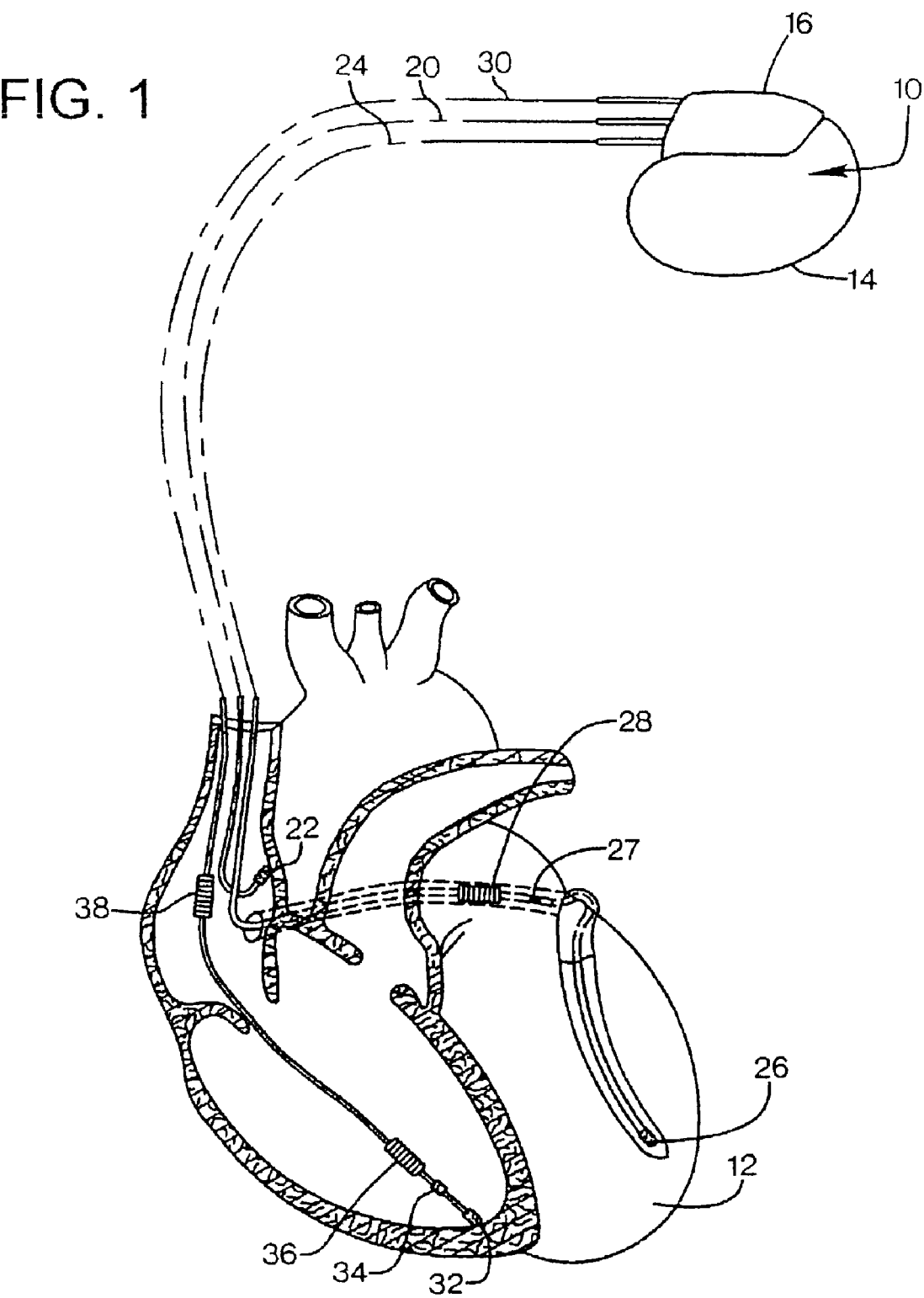
FIG. 1 is a simplified diagram illustrating an implantable stimulation device, in electrical communication with a patient's heart for delivering multi-chamber stimulation and shock therapy.

As shown in FIG. 1, there is a stimulation device 10 ore consistent with the preferred embodiment of the invention in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The device 10 has a hollow, sealed metal housing 14 containing the circuitry discussed below, and an attached header 16 to which the leads are connected.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculattire of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a Superior Vena Cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
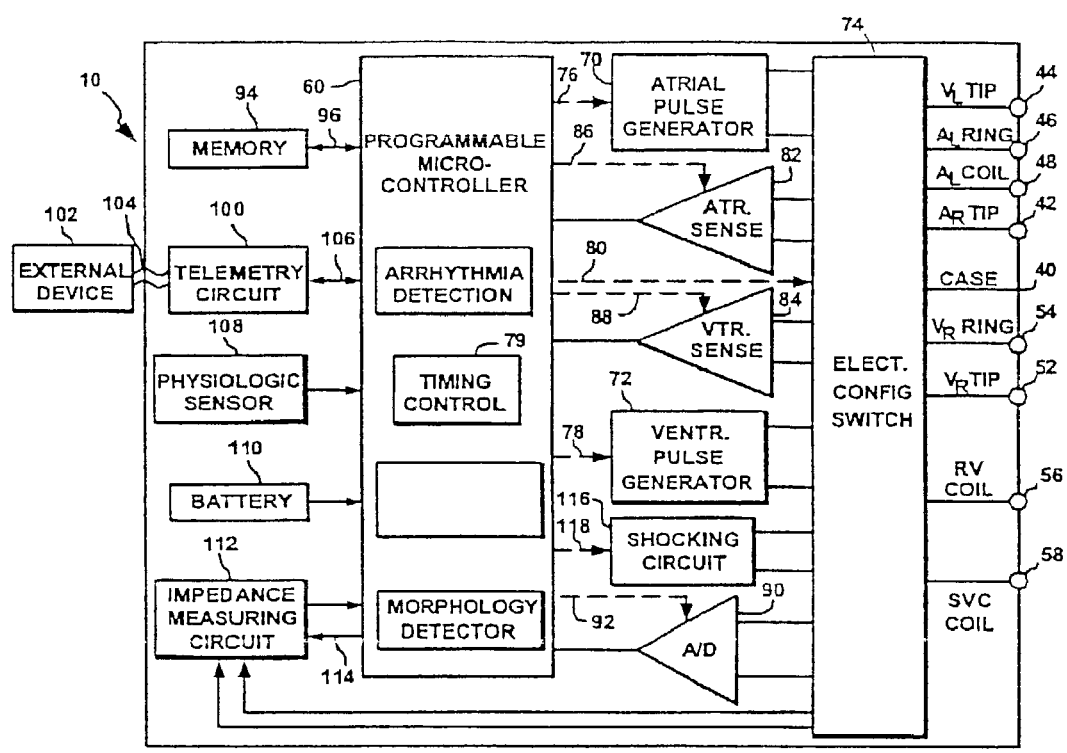
FIG. 2 is a functional block diagram of a multi-chamber implantable stimulation device according to the preferred embodiment illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can," "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconductioll (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. As will be discussed an illustrated below, the telemetry circuit is connected to an antenna for communicating with the external device via radio waves with a carrier frequency in the range of 10–15 MHz. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 μA), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (Up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
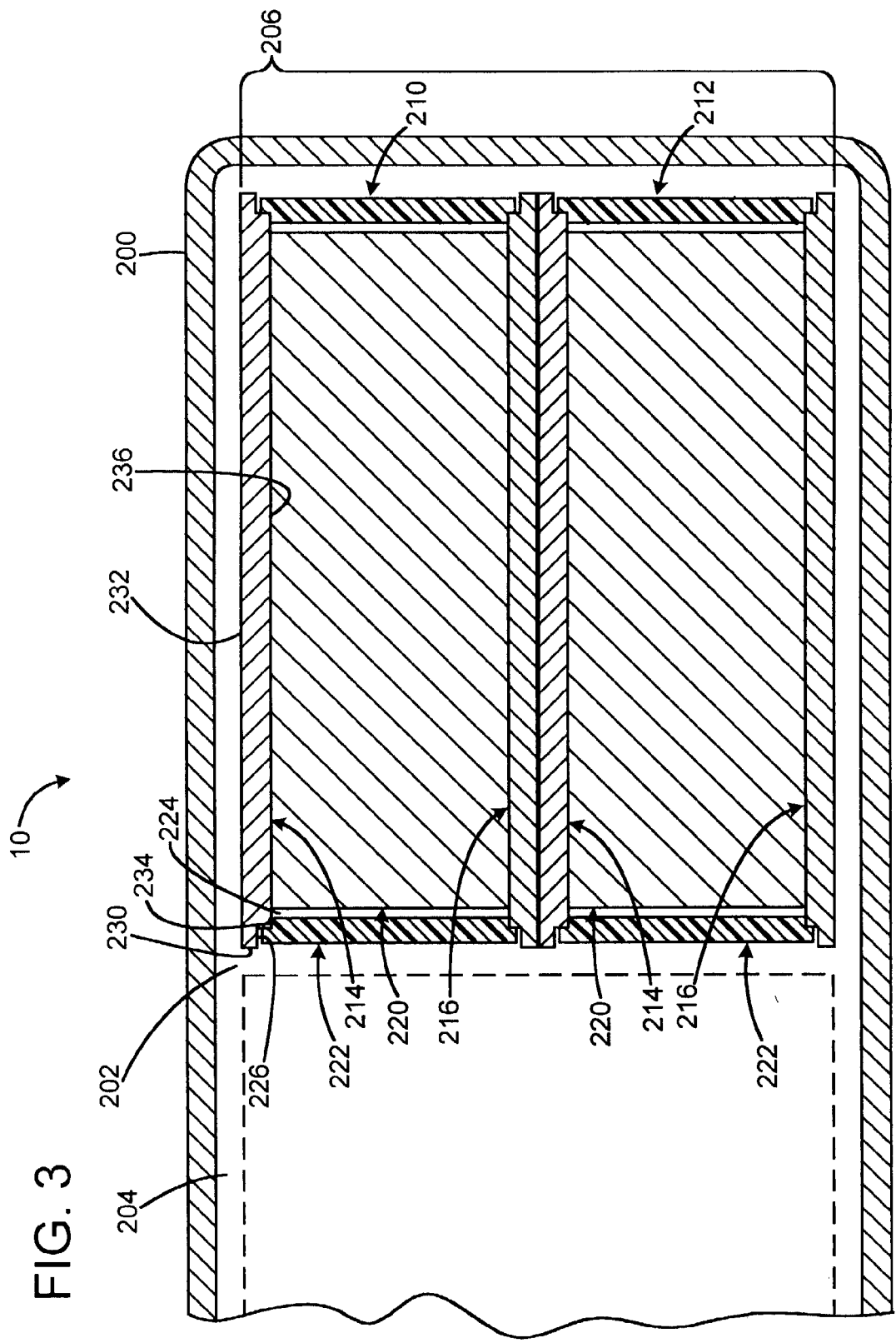
FIG. 3 is an enlarged sectional side view of the device of FIG. 1.

FIG. 3 illustrates the ICD 10 having a metal housing 200 defining a housing chamber 202 in which ICD circuitry 204 and a capacitor set 206 reside. The capacitor set includes two (or more, in alternative embodiments) capacitors 210, 212, which are identical to each other. Each capacitor has an anode plate 214 and a cathode plate 216, spaced apart in parallel to each other with a capacitor element 220 closely contained therebetween. A plastic peripheral housing band 222 extends about the periphery of each capacitor, joining the edges of the plates to define a leak-proof chamber 224 containing the capacitor element.

The shape of each capacitor is that of a flat body with opposed parallel major surfaces joined by a narrow peripheral band. The anode plate and cathode plates form the major surfaces of the capacitor in that they are the two largest surfaces of the body. As major surfaces, they collectively comprise a majority of the surface area of the body, with the peripheral band comprising well less than half of the body's surface area. Moreover, a body with two opposed major surfaces will have a thin profile, with a thickness less than the length or width of the major surfaces.

Each anode and cathode plate is a thin metal sheet of stainless steel or aluminum, with a thickness of 0.020 inch, and has a peripheral rabbet 226 that forms a 0.010 inch-wide step and flange 230 about the entire periphery of each plate. The flange overhangs the housing band 222, so that the exterior surface 232 of each plate extends over the entire area of the capacitor, and so that no portion of the capacitor extends beyond the plane defined by this surface.

The housing band 222 also defines a rabbet 234 extending about the entire periphery of the band at each edge, facing the interior direction. The band's rabbet is sized to closely receive the rabbeted portion of the plate. The interior surface 236 of each plate rests against the shoulder of the band's rabbet. The housing band 222 is formed of any suitable thermoplastic or rigid insulating material, including polypropylene, polyethylene, polyimide, polyetherimide, and acetyl. A leak-proof seal between the plates and the band is provided by an interference fit with the plates 214 and 216. An adhesive or sealant may supplement the seal.

As assembled, the anode plate 214 of the upper capacitor 210 is connected by a contact (not shown) to the ICD circuitry 204. The cathode plate 216 of capacitor 210 rests flat against the exterior surface of the anode plate 214 of capacitor 212. The cathode plate 216 of capacitor 212 contacts a contact (not shown) connected to ICD circuitry 204. In the preferred embodiment, the contact is a flex circuit portion with a conductive trace or pad contacting the plate and extending to the device circuitry, and an insulating Kapton sheet against the device housing 200 to electrically isolate the plate from the housing. To avoid contact between the plates and the device housing, an insulating boot (not shown) formed of thin plastic may wrap about the capacitors.

Figure 4:
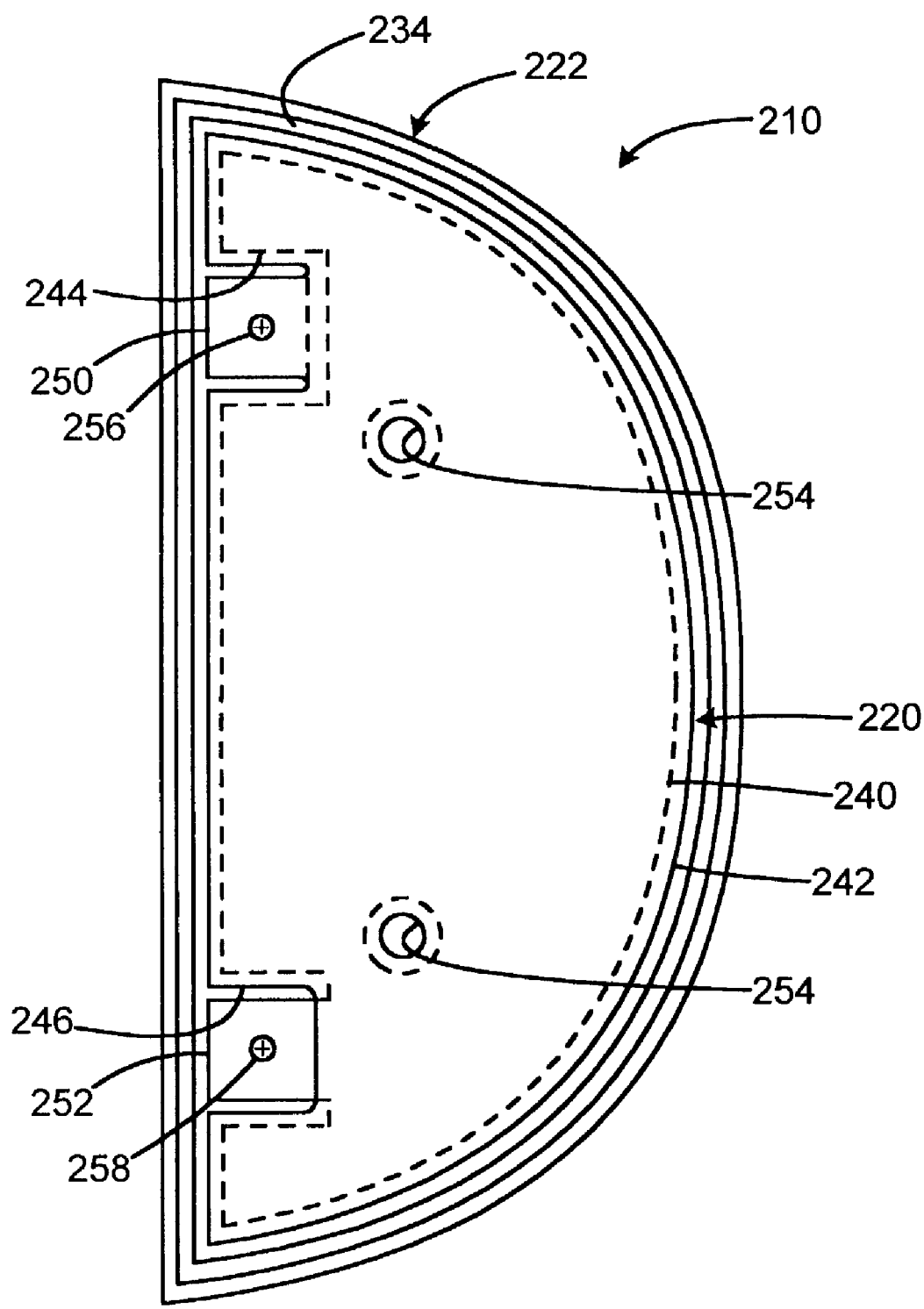
FIG. 4 is an enlarged plan view of a capacitor according to the preferred embodiment.

FIG. 4 shows an exemplary capacitor 210 seen in plan view with one plate removed to expose the capacitor element 220. The capacitor element is a stack of flat sheets, essentially with alternating anode sheets 240 and cathode sheets 242, separated by separators as discussed below. All components share the same peripheral profile (in this embodiment, a crescent shape for physiologic comfort with a straight side and a curved side) to maximize capacitance per unit volume with minimized wasted space. In alternative embodiments, the capacitor profile may be rectangular (if in the middle of a device) or any other suitable shape. The band 222, lower plate 216, and sheets 240 and 242 all share the profile shape.

The anode sheets 240 are all identical to each other, and each defines an anode cutout 244 on one edge location. Each of the cathode sheets 242 defines a similar cathode cutout 246 at a different location. The cathode sheets each have a cathode tab 250 registered with the anode cutout, and the anode sheets each have an anode tab 252 registered with the cathode cutout Adequate clearance is provided so that the edges of the tabs do not contact the opposite counterpart sheet edges at the cutouts. Separator sheets are coextensive with the cathode sheets (or slightly over sized.) The cathode sheets extend beyond the anode sheets to prevent electrical contact or arcing. A pair of registration holes 254 provides alignment features during assembly of the stack, with the anode layers having larger holes that have adequate clearance from the edges of the cathodes and separator layers. Although the anode layer peripheries are retracted from the peripheries of the cathode layers, and are unlikely to contact the housing band, the use of a non-conductive housing band permits this clearance to be minimal (or eliminated in alternative embodiments). This reduces device volume, and the only clearance requirements are between the cathode and anode sheet edges, which are readily aligned with tight tolerances, unlike the housing components and assembly process, which normally has less precise tolerances than the die-cutting or photolithographic process used to manufacture the sheets.

The cathode tabs 250 are electrically connected to each other and to the cathode plate by a resistance or ultrasonic spot weld 256, as are the anode tabs connected to each other and to the anode plate by a laser resistance or ultrasonic spot weld 258.

Figure 5:
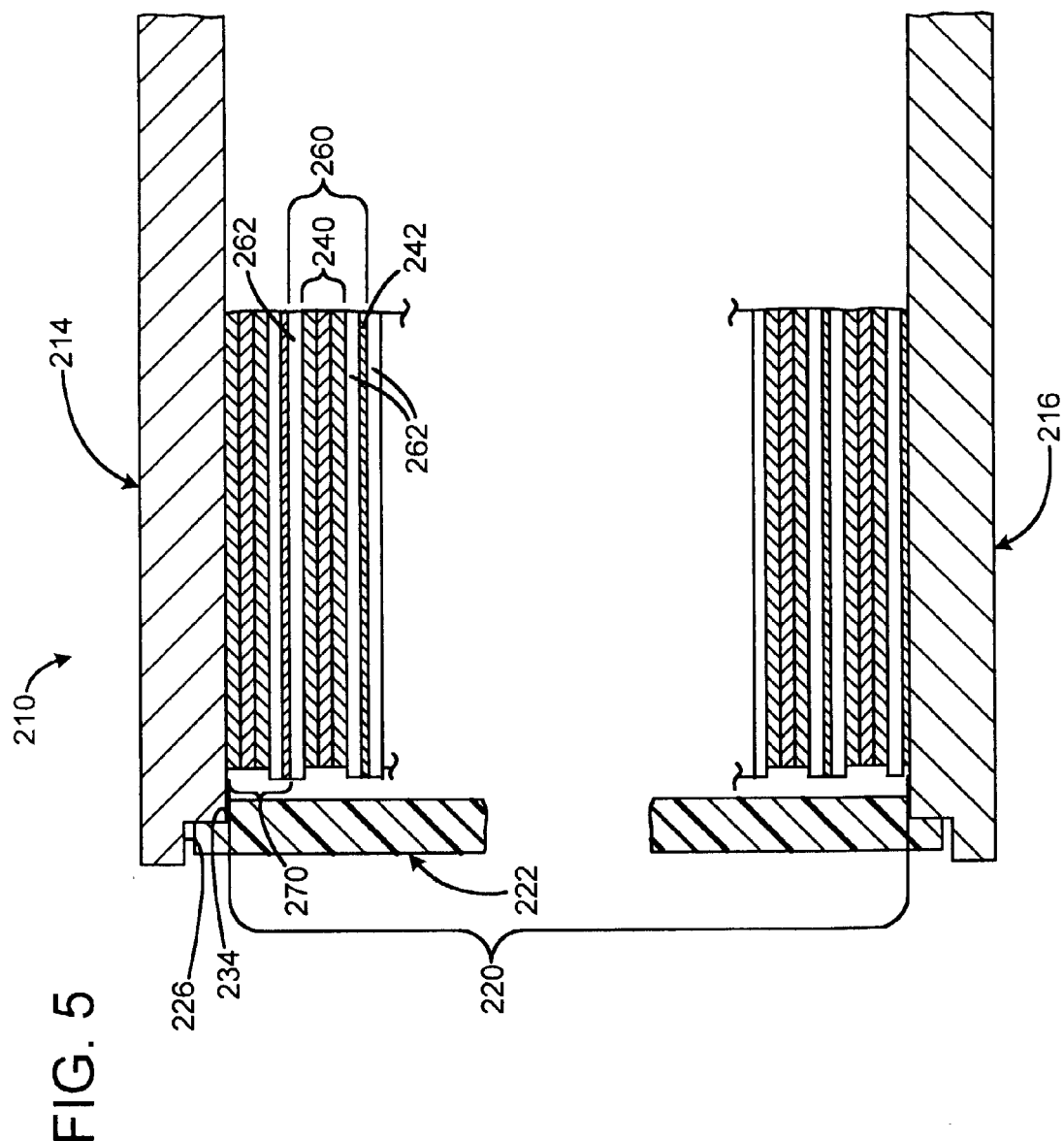
FIG. 5 is an enlarged sectional side view of the capacitor of FIG. 4.

FIG. 5 shows the arrangement of cathode and anode sheets in greater detail. To facilitate manufacturing, the sheets are arranged on modules or groups 260. Each module has a central anode layer 240 that may be formed of several sheets of highly etched foil to provide maximum surface area and capacitance per unit volume. The anode layer is covered on both faces by separator sheets 262, with a cathode foil sheet 242 overlaying one separator sheet. As illustrated, the separators and cathode sheets extend peripherally beyond the anode sheet edges. The modules are stacked in a suitable number to provide the needed charge storage capacity.

In the preferred embodiment triple anode design, there are 13 modules, including the module 270 nearest the anode plate. This provides a capacitance of 16.7 µF for each capacitor, at 415V maximum useful voltage. The total capacitance is 200 µF. The anode elements are 0.0025 inch thick, and formed of highly etched pure aluminum sheet. The cathode foil is 0.0005 inch thick, formed of pure aluminum with an inorganic oxide layer on each side. The separator layers are 0.001 inch thick, formed of polypropylene or paper. The overall stack thickness is 0.129 inch, and the stack closely fits within the chamber defined between the plates. The preferred embodiment capacitor has an approximate length of 2.08 inch, a width of 0.74 inch, and a thickness of 0.170 inch.

In alternative embodiments using conventional double or single anode capacitor technology such as used for camera flash units, three capacitors of lesser thickness and having a working voltage of 250V may be used to provide adequate total voltage to meet the 750V needs of the ICD circuitry. In other alternatives, the stack of flat anode and cathode layers may be replaced by a slug capacitor element.

Figure 6:
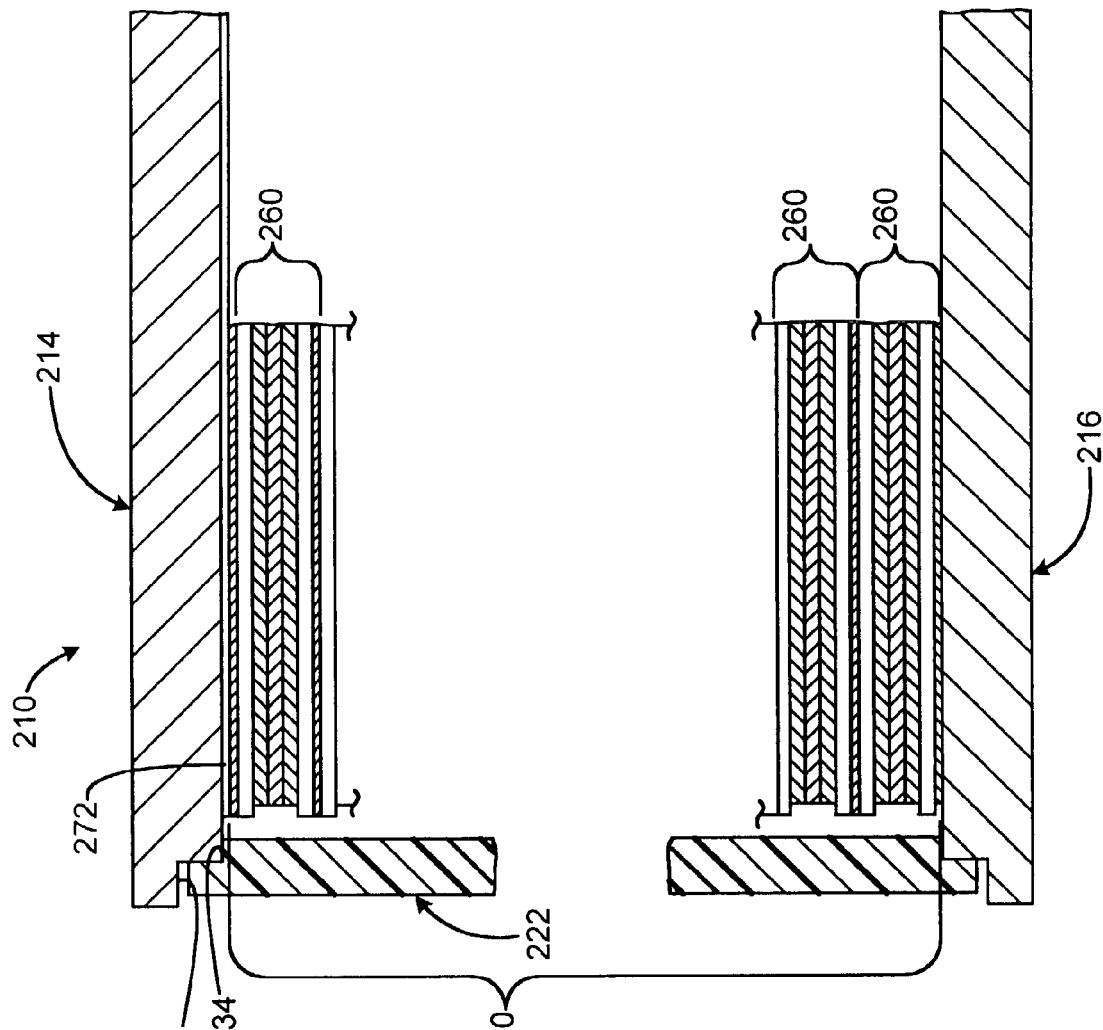
FIG. 6 is an enlarged sectional side view of a capacitor according to an alternative embodiment of the invention.

Returning to FIG. 5, module 270 is different from the other modules because it lacks the cathode layer that would otherwise contact the anode plate 214 and render the capacitor non functional. In this embodiment, the anode layer of the module directly contacts the plate, providing redundant electrical contact to supplement the welded connection between the anode tabs and the anode plate. The cathode layer of the module closest to the cathode plate provides similar supplementary electrical contact. In an alternative embodiment shown in FIG. 6, the module nearest the anode plate is a standard module 260, and an insulating layer 272 formed of polyamode is positioned between the uppermost cathode layer and the anode plate.

While described in terms of a preferred embodiment, the invention need not be so limited.

The invention claimed is:

1. An electrolytic capacitor comprising:
   a flat anode contact plate forming a first capacitor housing portion;
   a flat cathode contact plate parallel to and spaced apart from the anode contact plate and forming a second capacitor housing portion; and
   a planar charge storage element closely received between the contact plates, the planar charge storage element comprising a stack of interleaved flat anode sheets and flat cathode sheets, and the flat anode sheets and the flat cathode sheets disposed parallel to the flat anode contact plate and the flat cathode contact plate;
   wherein the cathode sheets are commonly electrically connected to the cathode contact plate, and the anode sheets are commonly electrically connected to the anode contact plate.

2. The capacitor of claim 1 including a non-conductive housing portion extending about the peripheries of the contact plates to define an enclosed chamber containing the charge storage element.

3. The capacitor of claim 1 wherein each of the contact plates has a conductive surface facing away from the charge storage element.

4. The capacitor of claim 3 wherein the conductive surfaces of the plates extend over substantially the entire exposed areas of the plates.

5. The capacitor of claim 1 wherein at least one of the contact plates is a metal sheet.

6. The capacitor of claim 1 wherein the stack comprises a plurality of sheet modules, each module including an anode sheet sandwiched between a pair of cathode sheets, with interleaved separators between each of the cathode sheets and the anode sheet.

7. The capacitor of claim 6 including an insulating layer separating the anode plate from the cathode sheet of the sheet module adjacent to the anode plate.

8. The capacitor of claim 6 wherein the sheet module adjacent to the anode plate has only a single cathode sheet separated from the anode plate by the anode sheet.

9. The capacitor of claim 6 wherein the anode sheet comprises three sheets of etched foil, and wherein a first face of separator sheets are disposed on both faces of the anode sheet and wherein a cathode sheet is disposed on a second face of each of the separator sheets.

10. The capacitor of claim 6 wherein each of the sheet modules are electrically connected in parallel.

11. The capacitor of claim 1 wherein the overall thickness of the capacitor is defined by the exposed major surfaces of the cathode and anode plates.

12. The capacitor of claim 1 wherein adjacent anode sheets are directly contacting, and wherein adjacent cathode sheets are directly contacting.

13. The capacitor of claim 1 wherein each of the anode sheets defines an anode cutout on one edge location, and wherein each of the cathode sheets defines a cathode cutout at a different location, wherein each of the cathode sheets has a cathode tab registered with the anode cutout, wherein each of the anode sheets has an anode tab registered with the cathode cutout, wherein the cathode tabs of adjacent cathodes sheets are directly contacting, and wherein the anode tabs of adjacent anode sheets are directly contacting.

* * * * *